(12) United States Patent
Koenig

(10) Patent No.: US 8,223,005 B2
(45) Date of Patent: Jul. 17, 2012

(54) DRIVER INFORMATION AND DIALOG SYSTEM

(75) Inventor: Winfried Koenig, Pfinztal (DE)

(73) Assignee: Robert Bosch GmbH, Stuttgart (DE)

( * ) Notice: Subject to any disclaimer, the term of this patent is extended or adjusted under 35 U.S.C. 154(b) by 350 days.

(21) Appl. No.: 12/312,257

(22) PCT Filed: Sep. 5, 2007

(86) PCT No.: PCT/EP2007/059302

§ 371 (c)(1),
(2), (4) Date: Jan. 20, 2010

(87) PCT Pub. No.: WO2008/052829

PCT Pub. Date: May 8, 2008

(65) Prior Publication Data

US 2010/0127843 A1   May 27, 2010

(30) Foreign Application Priority Data

Nov. 3, 2006  (DE) .................... 10 2006 051 922

(51) Int. Cl.
*B60Q 1/00* (2006.01)
(52) U.S. Cl. .................... 340/439; 340/425.5; 340/540; 340/903
(58) Field of Classification Search ............... 340/425.5, 340/439, 540, 903; 701/123, 1, 200, 22, 701/23, 29; 702/182, 183, 188, 22
See application file for complete search history.

(56) References Cited

U.S. PATENT DOCUMENTS

| 4,706,072 | A | 11/1987 | Ikeyama | |
|---|---|---|---|---|
| 6,952,161 | B1 | 10/2005 | Williams | |
| 2002/0109602 | A1 | 8/2002 | Shinada | |
| 2002/0151297 | A1* | 10/2002 | Remboski et al. | 455/414 |
| 2005/0116829 | A1* | 6/2005 | Koenig et al. | 340/576 |
| 2005/0131597 | A1* | 6/2005 | Raz et al. | 701/29 |
| 2006/0287783 | A1* | 12/2006 | Walker | 701/29 |
| 2010/0191423 | A1* | 7/2010 | Koyama et al. | 701/42 |

* cited by examiner

*Primary Examiner* — Daryl Pope
(74) *Attorney, Agent, or Firm* — Kenyon & Kenyon LLP

(57) ABSTRACT

A driver information and dialog system disposed in a vehicle and relating to driver behavior data and driver condition data, having a data acquisition device and an input/output device, the output device informing the driver about a collecting, storage, use, processing, and or transmission of driver behavior data and driver condition data, and the input device allowing the driver to transmit his decision consenting to or denying the collecting, storage, use, processing, and/or transmission of driver behavior data and driver condition data. Furthermore, a method for informing the driver and for dialog with the driver regarding driver behavior data and driver condition data collected in a vehicle, the driver being informed about the collecting, storage, use, processing, and/or transmission of driver behavior data and driver condition data, and the driver making decisions about the collecting, storage, use, processing, and/or transmission of driver behavior data and driver condition data.

9 Claims, 2 Drawing Sheets

DRIVER INFORMATION AND DIALOG SYSTEM

BACKGROUND INFORMATION

Monitoring systems that acquire data about the behavior of the driver and/or data about the condition of the driver of motor vehicles are known from the related art. For example, such data include the driving behavior of the driver, the route driven, the condition of the driver, his gestures, facial expression, etc. Furthermore, sensing systems, which sense the dynamics of the vehicle; data from navigation systems; data from assistance systems; and data from imaging sensors are evaluated. In the broadest sense, these systems are used to detect early and to eliminate possible driving errors of the driver, or to warn the driver about possible driving errors, and/or to alert the driver to the circumstances that have a negative influence on driving safety, such as fatigue, for example. The data acquisition and data conditioning is extremely complex. The storage of data acquired in this manner frequently takes place in the vehicle, for example, for the documentation for questions regarding warranty; some data are also transmitted to the outside. Due to the complexity of the systems, it is usually not possible for the driver to find out which data are acquired, how these relate to his behavior, which of these are stored, and how these data are further processed.

SUMMARY OF THE INVENTION

An objective of the present invention is to allow the driver to make a decision in an easily comprehensible and clear manner, regarding which data are acquired, stored, and/or provided to others.

To this end, a driver information and dialog system disposed in a vehicle and relating to driving behavior data and driving condition data is provided, having a data acquisition device and an input/output device, the output device informing the driver about the collection, storage, use, processing, and or transmission of driver behavior data and driver condition data, and the input device allowing the driver to transmit his decision consenting to or denying the collecting, storage, use, processing, and/or transmission of driver behavior data and driver condition data. Accordingly, the opacity of the "blackbox" system, which opacity until now has existed for the driver of the vehicle, is penetrated in favor of a free decision of the driver, the driver being able to decide himself with regard to driver behavior data and driver condition data whether these are collected at all, whether they are possibly stored, used, processed, and/or transmitted. In this context, the driver retains the complete control over the system.

In one preferred specific embodiment, the data acquisition device acquires data from a navigation system, at least one driving condition sensor, at least one driver assistance system, a driver monitoring sensor system, and/or a driver condition sensor system.

In another preferred embodiment of the system, the acquired data are supplied to an evaluation system. The evaluation system sets the acquired data in relation to each other and evaluates it according to predefined criteria.

In another preferred embodiment of the system, the present invention has a data transmission system for exchanging data with at least one stationary device. In this instance, the data approved by the driver are transmitted to a stationary device, possibly only when necessary. At the same time, it may also be possible to transmit data to the stationary device, in so far as this is necessary and/or desired.

In another preferred specific embodiment, it is provided that the output device provides driver behavior information and/or driver condition information and/or makes suggestions to the driver as a function of at least one evaluation result of the evaluation system. In this specific embodiment, the driver does not have to make a decision blindly regarding the acquisition of data or its further use, for example, storage, but rather may do this as a function of at least one already existing evaluation result, the driver information and dialog system also making suggestions to him in a particularly preferred specific embodiment. For example, in this context, it is possible to provide information, in a clearly comprehensible form, to the driver about the data collected in the vehicle, the stored data possibly to be transmitted to external locations; to classify it as a function of already acquired data; and to make useful suggestions to the driver with the aid of the result.

Furthermore, the present invention relates to a method for informing the driver and for dialog with the driver, regarding driver behavior data and driver condition data collected in a vehicle. It is provided that the driver is informed about the collecting, storage, use, processing, and/or transmission of driver behavior data and driver condition data, and the driver makes a driver decision about the collecting, storage, use, processing, and/or transmission of the driver behavior data and driver condition data. In contrast to the method known from the related art for collecting such data, the driver is allowed to make the decision with regard to each individual piece of data or data class, whether it is to be collected, stored, used, processed, and/or transmitted at all.

DETAILED DESCRIPTION

Figure 1:
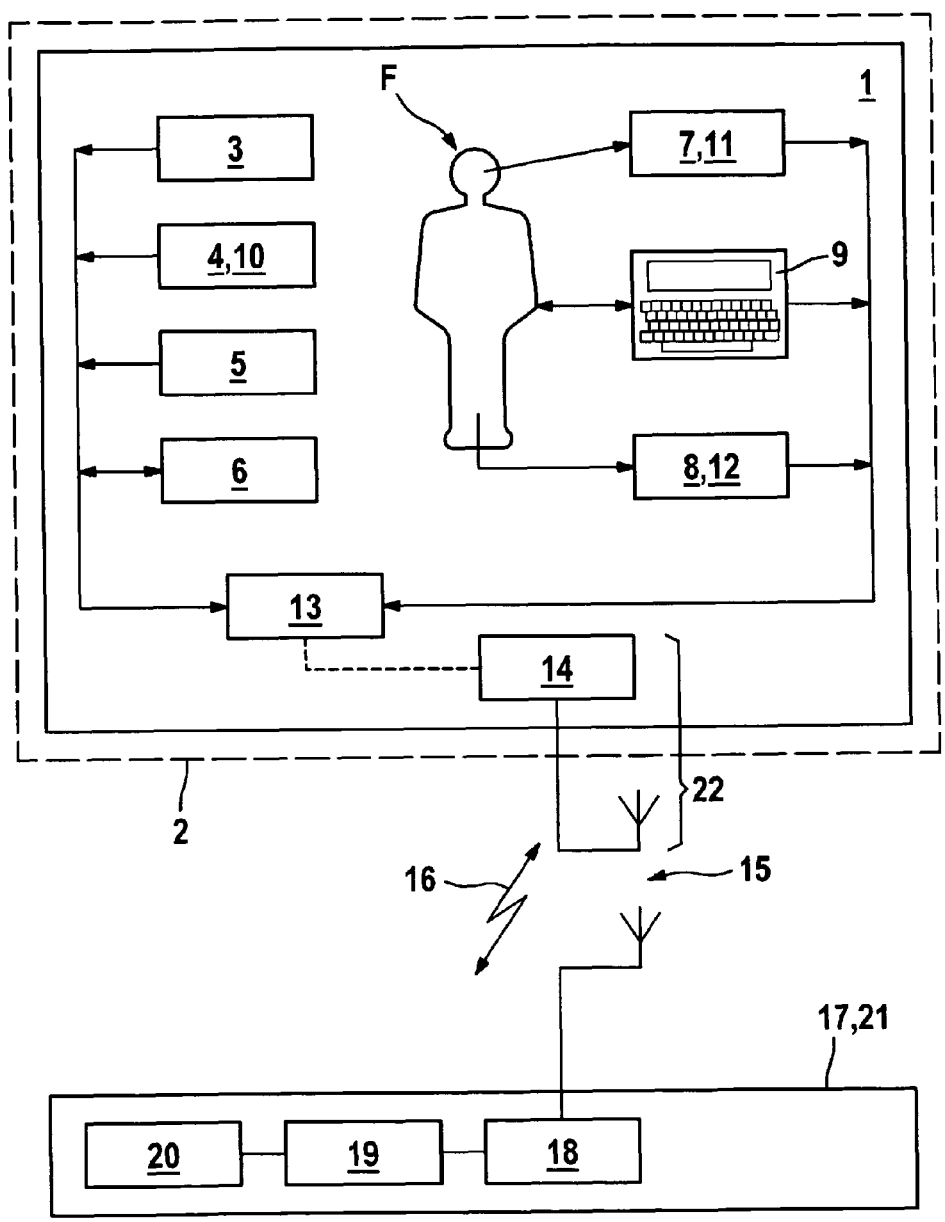
FIG. 1 shows a schematic representation of a driver information and dialog system.

FIG. 1 shows in a schematic representation/block diagram, a driver information and dialog system 1 of a motor vehicle 2. Driver information and dialog system 1 includes a navigation system 3, dynamics sensors 4, driver assistance systems 5, and a data memory 6 for data storage for data of navigation system 3, dynamics sensors 4, and driver assistance systems 5 within the vehicle. Driver information and dialog system 1 also includes an imaging sensor system 7, a driver parameter acquisition 8, and an input/output device 9. In this context, dynamics sensor 4 is designed in particular as a driving condition sensor 10, imaging sensor system 7 as driver monitoring sensor system 11, and driver parameter acquisition 8 as driver condition sensing system 12. The data exchange between the individual components takes place in part in a bidirectional manner, in particular with regard to data memory 6 and input/output device 9. The data merge together in a monitoring system 13, with which a transmitter/receiver 14 is connected as data transmission system 22 for exchanging data via an air interface 15, that is, in particular via radio 16, to a stationary monitoring center 17, for example, in which center the data are in turn received by a transmitter/receiver unit 18 and processed using a computer 19, and stored in a stationary data memory 20. In this context, the stationary monitoring center as stationary device 21 is not a necessary prerequisite for driver information and dialog system 1; however, its presence makes the presence of a driver information and dialog system desirable in motor vehicle 2 for a driver F.

Figure 2:
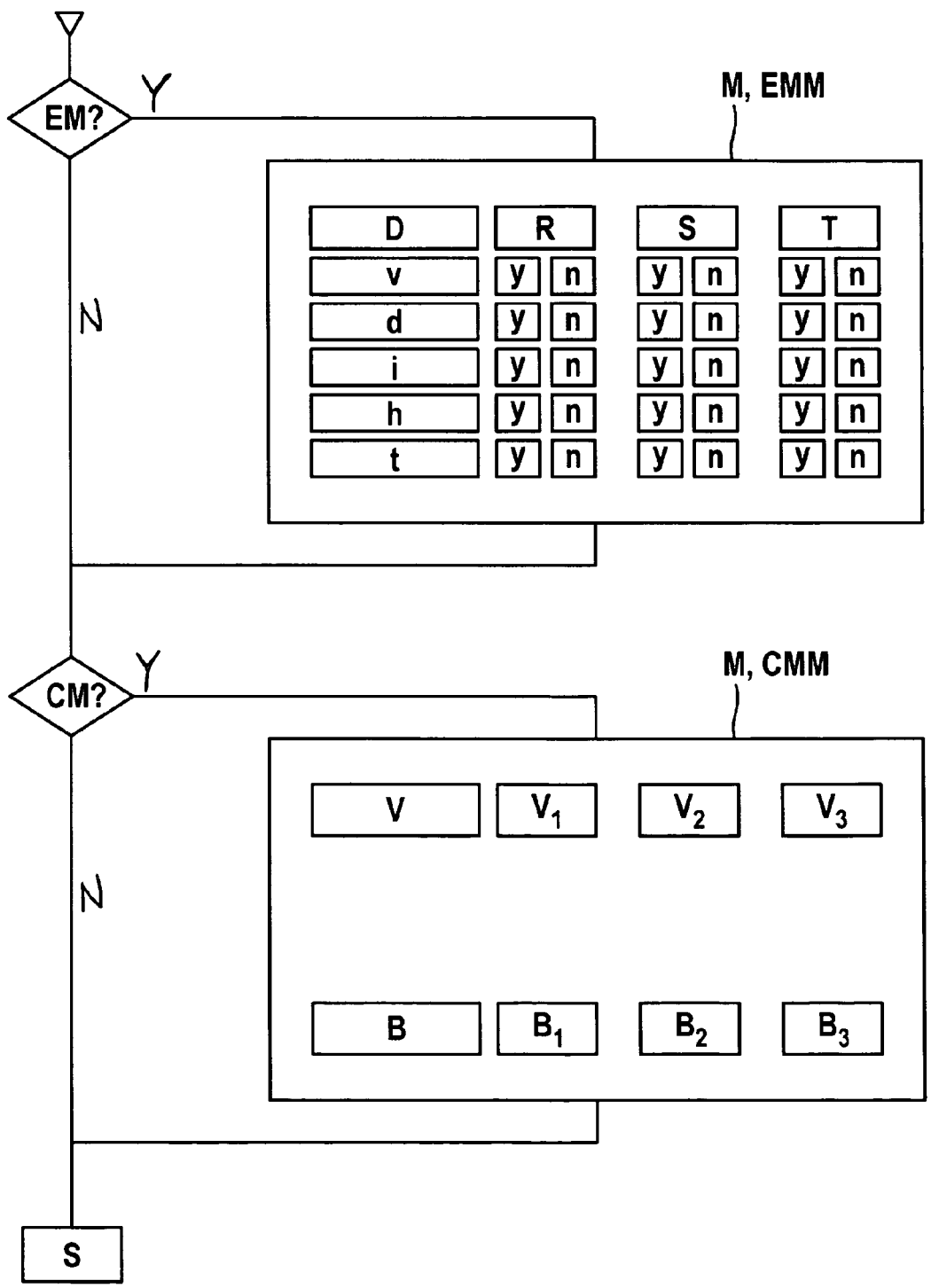
FIG. 2 shows a dialog and decision path for making a driver decision according to the method.

FIG. 2 shows a dialog and decision path for making a driver decision according to the method. In one illustration of input/output device 9, which is not shown in this instance, driver F receives the information and decision structure set forth below: Driver F is prompted to decide whether he wants to make the driver decision in an expert mode EM or in a comfort mode CM, comfort mode CM always being switched on when driver F does not explicitly select expert mode EM. As an alternative to this, it is possible to completely turn off the system, or to prevent completely a collecting or any type of further processing of data, if neither expert mode EM nor comfort mode CM is selected; this method position, in this instance labeled as stop S in the method sequence, may be occupied with additional decision structures or actions designed or selected as a function of the driver information and dialog system for the execution of the method. Expert mode EM and comfort mode CM differ with regard to the information and decision structure shown to driver F for the purpose of informing and of carrying out the driver decision, of matrix M, which in the expert mode is implemented as expert mode matrix EMM and in the comfort mode is implemented as comfort mode matrix CMM. In expert mode matrix EMM, many more decision options are provided to driver F than in comfort mode matrix CMM, in which the decisions are reduced essentially to two type classes in this instance, which allow driver F to make settings particularly comfortably depending on the categorization, for example. In comfort mode matrix CMM, he makes a decision regarding only the degree of confidentiality V, and regarding whether driver information and dialog system 1 is to advise him with regards to roadworthy driving, that is, regarding the scope of advising B to be performed by driver information and dialog system 1. In confidentiality V, driver F makes decisions regarding the level of confidentiality, which may be set as low confidentiality $V_1$, middle confidentiality $V_2$, and high confidentiality $V_3$; the driver behavior data and driver condition data to be collected, stored, used, processed, and/or transmitted by driver information and dialog system 1 are selected automatically by the driver information and dialog system in accordance with the rating and categorization carried out, in accordance with the selected confidentiality level. For example, in high confidentiality level $V_3$, driver information and dialog system 1 is not allowed to transmit driver behavior data and driver condition data, in particular via an air interface 15 to a stationary monitoring center 17. On the other hand, if driver F chooses low confidentiality $V_1$ in his driver decision, the collecting, storing, use, processing, and/or transmission of driver behavior data and driver condition data is allowed to the full extent.

Additionally, driver F may make a decision about advising B desired from the driver information and dialog system, regarding roadworthy driving as a function of the acquired driver behavior data and driver condition data, it being possible for him to choose between the levels "no advising" B1, "tolerant advising" B2, and "exact advising" B3, for example. Depending on the degree of desired advising intensity B1, B2, or B3, as a function of the acquired driver behavior data and driver condition data, driver information and dialog system 1 provides advice and tips, which relate to the driving safety of the driver and which are to increase it. In particular, in this instance it is provided that signs of fatigue of driver F and driving techniques that lack concentration be indicated. In a level in which no advising B1 is selected, no corresponding tips and advice are provided to driver F. In a level in which tolerant advising B2 is desired, driver F is made aware of physical tiredness and the danger of losses of function (for example, to avoid momentary drowsiness), whereas, for example, in the level in which exact advising B3 is desired, driver F may be made aware of a multitude of factors that depend on data acquired and processed by driver information and dialog system 1, for example, even psychological factors, which even include aggressive driving style, irritation, etc., for example, these driver conditions being obtained and determined in a complex manner from a multitude of driver behavior data and condition data from the driver information and dialog system.

In expert mode EM, driver F has the option of making a differentiated decision in expert mode matrix EMM. To this end, selection options relating to data D about speed v of his vehicle, the distance to preceding vehicle d, lane departure i, his circulation h, and the degree of his tiredness t are presented. These data D are acquired by the driver information and dialog system via in particular a driver monitoring sensor system 11 and/or a driver condition sensor system 12; additional parameters from additional standard vehicle sensors are added to this. With regard to every single piece of data D, a selection option is provided about the recording or acquiring R, the storing S, and the transmission T. In the decision groups for recording/acquiring R, for storing S, and for transmission T, for each piece of data, driver F may decide Yes y or No n with regard to speed v, the distance to preceding vehicle d, lane departure i, circulation h, and tiredness t of driver F. In contrast to the comfort mode, which groups and classifies the decision-relevant data in comfort mode matrix CMM, and only allows a decision regarding the level of confidentiality V and the level of desired advising B, in expert mode EM, driver F may make a differentiated decision in expert mode matrix EMM, according to which, for example, the recording of all data relating to speed v, distance to preceding vehicle d, lane departure i, circulation h, and tiredness t may be acquired (within the block about the recording/the acquiring R all selections are activated with Yes y); however, with regard to speed v, the distance to preceding vehicle d, and driver tiredness t, the driver does not desire a storage S and thus in this instance selects No n. With regard to all data D selected in the block record/store R, driver F does not desire a transmission to stationary devices 21, so that in block transmission T he selects No n with regard to all data T.

Of course, the design of the respective matrix M both in expert mode EM and in comfort mode CM may be modified depending on the requirements to be satisfied by the system and the selection freedom to be provided to driver F, all data that come into consideration, that are to be acquired and processed by the driver information and dialog system being presented.

What is claimed is:

1. A driver information and dialog system that is situated in a vehicle, comprising:
   a data acquisition device;
   an output device informing a driver of the vehicle about at least one of a collecting, storage, use, processing and transmission of driver behavior data and driver condition data; and
   an input device allowing the driver to transmit a decision of the driver consenting to or denying the at least one of the collecting, storage, use, processing, and transmission of driver behavior data and driver condition data, wherein the input device is configured for receiving a plurality of consent decisions that are inputtable in the alternative and that differ with respect to an amount of driver behavior data and an amount of driver condition data indicated to be at least one of collected, stored, used, processed, and transmitted.

2. The system according to claim 1, wherein the data acquisition device acquires data from at least one of (a) a navigation system, (b) at least one driving condition sensor, (c) at least one driver assistance system, (d) a driver monitoring sensor system, and (e) a driver condition sensor system.

3. The system according to claim 2, further comprising an evaluation system for receiving the acquired data.

4. The system according to claim 3, wherein the output device provides output to the driver in accordance with the amount of driver behavior data and the amount of driver condition data indicated by the decision, the output including at least one of (a) driver behavior information, (b) driver condition information, and (c) suggestions to the driver, as a function of at least one evaluation result of the evaluation system.

5. The system according to claim 1, further comprising a data transmission system for exchanging data with at least one stationary device.

6. The system according to claim 1, wherein the decision is customizable via a user interface of the input device, the user interface including a selectable option for a general scope of advising and a selectable option for a general level of confidentiality.

7. The system according to claim 1, wherein the decision is customizable via a user interface of the input device, the user interface including separate recording, storage and transmission options for each category in the following list of categories: vehicle speed, distance to a preceding vehicle, lane departure, driver circulation, and driver tiredness.

8. The system according to claim 1, wherein:
the decision is customizable via a user interface of the input device, the user interface presenting the driver with a selectable choice between an expert mode and a comfort mode;
the comfort mode includes a selectable option for a general scope of advising and a selectable option for a general level of confidentiality; and
the expert mode includes separate selectable recording, storage and transmission options for each category in the following list of categories: vehicle speed, distance to a preceding vehicle, lane departure, driver circulation, and driver tiredness.

9. A method for informing a driver of a vehicle and for having a dialog with the driver regarding driver behavior data and driver condition data, the method comprising:
informing the driver about at least one of a collecting, storage, use, processing, and transmission of driver behavior data and driver condition data in the vehicle; and
receiving a decision of the driver about the at least one of the collecting, storage, use, processing, and transmission of driver behavior data and driver condition data, wherein the decision is input via an input device that is configured for receiving a plurality of consent decisions that are inputtable in the alternative and that differ with respect to an amount of driver behavior data and an amount of driver condition data indicated to be at least one of collected, stored, used, processed, and transmitted.

* * * * *